(12) United States Patent
Kinlen et al.

(10) Patent No.: US 12,234,213 B2
(45) Date of Patent: Feb. 25, 2025

(54) REDUCTIVE DIMERIZATION OF FURFURAL VIA A CONTINUOUS PROCESS

(71) Applicant: The Boeing Company, Chicago, IL (US)

(72) Inventors: Patrick J. Kinlen, Fenton, MO (US); William F. Lyons, Normandy Park, WA (US)

(73) Assignee: THE BOEING COMPANY, Arlington, TX (US)

( * ) Notice: Subject to any disclaimer, the term of this patent is extended or adjusted under 35 U.S.C. 154(b) by 259 days.

(21) Appl. No.: 17/370,697

(22) Filed: Jul. 8, 2021

(65) Prior Publication Data

US 2022/0089557 A1 Mar. 24, 2022

Related U.S. Application Data

(60) Provisional application No. 63/082,681, filed on Sep. 24, 2020.

(51) Int. Cl.
| | | |
|---|---|---|
| *C07D 307/42* | (2006.01) | |
| *B01J 8/02* | (2006.01) | |
| *B01J 21/06* | (2006.01) | |
| *B01J 39/04* | (2017.01) | |
| *B01J 47/02* | (2017.01) | |
| *C25B 3/05* | (2021.01) | |
| *C25B 3/07* | (2021.01) | |
| *C25B 3/29* | (2021.01) | |

(52) U.S. Cl.
CPC ............ *C07D 307/42* (2013.01); *B01J 8/025* (2013.01); *B01J 21/063* (2013.01); *B01J 39/04* (2013.01); *B01J 47/02* (2013.01); *C25B 3/05* (2021.01); *C25B 3/07* (2021.01); *C25B 3/295* (2021.01); *B01J 2208/00831* (2013.01)

(58) Field of Classification Search
CPC ....... C07D 307/42; B01J 8/025; B01J 21/063; B01J 39/04; B01J 47/02; B01J 2208/00831; C25B 3/05; C25B 3/07; C25B 3/295
See application file for complete search history.

(56) References Cited

FOREIGN PATENT DOCUMENTS

| NO | 115286 B | * | 9/1968 | |
|---|---|---|---|---|
| WO | WO 2013/135869 A1 | | 9/2013 | |
| WO | WO-2017106916 A1 | * | 6/2017 | ............ B01F 25/431 |

OTHER PUBLICATIONS

Chadderon et al. J. Am. Chem. Soc. 2017, 139, 40, 14120-14128. (Year: 2017).*
Annunziata et al. Eur. J. Org. Chem., 1999: 3369-3374. (Year: 1999).*

(Continued)

*Primary Examiner* — Matthew P Coughlin
*Assistant Examiner* — Ashli Ariana Chicks
(74) *Attorney, Agent, or Firm* — Moore IP Law (57) ABSTRACT

Described herein are methods for the continuous preparation of 1,2-di(furan-2-yl)ethane-1,2-diol from furan-2-carbaldehyde. The methods can proceed chemically or electrochemically. In certain examples, the methods further comprise the application of a static mixer. The present methods produce 1,2-di(furan-2-yl)ethane-1,2-diol in greater yield, purity, chemoselectivity, and stereoselectivity than traditional batch methods.

21 Claims, 6 Drawing Sheets

(56) References Cited

OTHER PUBLICATIONS

Sotto et al. J. Org. Chem. 2015, 80, 12, 6375-6380. (Year: 2015).*
Li et al. Journal of Chemical Research. 2005;2005(6):361-363. (Year: 2005).*
Nador et al. Reductive coupling of carbonyl compounds promoted by cobalt or titanium nanoparticles. ARKIVOC 2011 (vii) 312-326. (Year: 2011).*
Arenas et al. 2020 J. Electrochem. Soc. 167 023504. (Year: 2020).*
Zhao et al. Pinacol Coupling Reactions Catalyzed by Active Zinc. Chinese Chemical Letters vol. 16, No. 11, pp. 1459-1462, 2005. (Year: 2005).*
Shang et al. Electrohydrodimerization of biomass-derived furfural generates a jet fuel precursor. Green Chem., 2020, 22, 5395- 5401. (Year: 2020).*
Anibal et al. ACS Catalysis 2020 10 (19), 11643-11653. (Year: 2020).*
Barden et al., "Stereoselective Pinacol Coupling in Aqueous Media," J. Am. Chem. Soc., 118, 5484-5485, (1996).
Bian et al., "Coupling Reactions of Aromatic Aldehydes Using Manganese under Ultrasound Irradiation," Chinese Journal of Organic Chemistry, 24(7):828-839, (2004).
Bian et al., "Reductive Coupling of Aromatic Aldehydes Using Zinc Powder in Aqueous Sodium Hydroxide under Ultrasound," Chinese Journal of Synthetic Chemistry, 12:429-431, 434, (2004).
Bian et al., "Study on the Electrosynthesis of Pincols, " Chinese Journal of Organic Chemistry, 26(8):1130-1132, (2006).
Bian et al., "Studies on synthesis of vicinal diol catalyzed by zinc powder in water," Chemical Research and Application, 19(6) 683-686, (2007).
Bian et al., "Study on the Synthesis of Pinacol Using Gallium in Aqueous Media," Journal of Hebei Normal University, Natural Science Edition, 31(6):772-774, (2007).
Bian et al., "Reductive Coupling of Aromatic Aldehydes Induced by Lanthanum in Aqueous Media," Huaxue Tongbao, 71(10):793-796 (2008).
Bian et al., "Reductive Coupling of Aromatic Aldehydes With Neodymium in Aqueous Media," Journal of Hebei University, Natural Science Edition, 31(6):623-626, (2011).
Billamboz et al., "First Pinacol Coupling in Emulsified Water: Key Role of Surfactant and Impact of Alternative Activation Technologies," Chem Sus Chem 8:1664-1675, (2015).
Gallezot, P., "Conversion of biomass to selected chemical products," Chem. Soc. Rev., 41:1538-1558, (2012).
Gansäuer, A., "Pinacol coupling of aromatic aldehydes catalysed by a titanocene complex: a transition metal catalysed radical reaction," Chem. Commun., 5:457-458, (1997).
Gansäuer et al., "Titanocene-Catalyzed Pinacol Couplings: Reagent-Controlled Transition-Metal-Catalyzed Radical Reactions," Eur. J. Org. Chem. 9:1923-1927, (1998).
Grugel et al., "A Highly Streoselective C—C Coupling of Aldehydes Forming Glycols Via A Stannylenoid Reaction," Tetrahedron Letters No. 31, 2847-2850, (1978).
Handa et al., "A highly steroselective pinacolization of aromatic and α, β-unsaturated aldehydes mediated by titanium(III)-magnesium(II) complex," Tetrahedron Letters No. 28, 5717-5718, (1987).
Huang et al., "Production of high quality fuels from lignocellulose-derived chemicals: a convenient C—C bond formation of furfural, 5-methylfurfural and aromatic aldehyde," RSC Advances, 2:11211-11214, (2012).
Li et al., "Reductive Coupling of Aromatic Aldehydes Using Low Valent Titanium Complexes under Ultrasound Irradiation," Chinese Journal of Organic Chemistry, 23(12):1428-1431, (2003).
Li et al., "Pinacol coupling of aromatic aldehydes and ketones by $TiCL_4$—Mg—ThF under ultrasound irradiation," Journal of Chemical Research, 6:361-363, (2005).
Nador et al., "Reductive coupling of carbonyl compounds promoted by cobalt or titanium nanoparticles," Org Chem Arg, VII:312-326, (2011).

Sotto et al., "Selective Pinacol Coupling on Regenerable Supported Acids in Sole Water," JOC, 80(12):6375-6380, (2015).
Takkellapati, S. et al., "An overview of biorefinery-derived platform chemicals from a cellulose and hemicellulose biorefinery," Clean Technologies and Environmental Policy, 20(7):1615-1630, (Sep. 2018).
Xu et al., "Vanadium-Catalyzed Pinacol Coupling Reaction in Water," J. Org. Chem., 70:8594-8596, (2005).
Yamamoto et al., "Diastereoselective Inter- and Intramolecular Pinacol Coupling of Aldehydes Promoted by Monomeric Titanocene(III) Complex $Cp_2TiPh$," J. Org. Chem., 66:3865-3870, (2001).
Zang et al., "Pinacol coupling of aromatic aldehydes and ketones using Zn—$ZnCl_2$ under ultrasound," Indian Journal of Chemistry, 41b:1078-1080, (2002).
Zhang et al., "Magnesium in water: simple and effective for pinacol-coupling," J. Chem. Soc., Perkin Trans. 1, 3131-3132, (1998).
Bandini et al., "Highly Diastereoselective Pinacol Coupling of Aldehydes Catalyzed by Titanium-Schiff Base Complexes," Tetrahedron Letters, 40:1997-2000, (1999).
Bian et al., "Reductive Coupling Reactions of Aromatic Aldehydes by Using Aluminum under Microwave Irradiation," Chinese Journal of Organic Chemistry, 31(10):1695-1697, (2011).
Botte, "Electrochemical Manufacturing in the Chemical Industry," The Electrochemical Society Interface, https://www.electrochem.org/dl/interface/fal/fal14/fal14_p049_055.pdf, 49-55, (Fall 2014; retrieved Apr. 9, 2024).
Corma et al., "Chemical Routes for the Transformation of Biomass into Chemicals," Chem. Rev., 107:2411-2502, (2007).
Csiro, "Catalytic Static Mixers—CSMs," FloWorks, https://research.csiro.au/floworks/research/catalytic-static-mixers/, 2 pages, (retrieved Apr. 9, 2024).
Deng et al., "First Magnesium-mediated Carbonyl Benzylation in Water," Chinese Journal of Chemistry, 22:747-750, (2004).
DÖBereiner, "On the medical and chemical application and the beneficial preparation of formic acid," Reports of the German Chemical Society, 3:141-146, (1832).
Ebert, "Furfural: Future Feedstock For Fuels and Chemicals," Biomass Magazine, http://www.biomassmagazine.com/articles/1950/furfural-future-feedstock-for-fuels-and-chemicals, 2 pages, (retrieved Apr. 9, 2024).
Farm Energy, "Reactors for Biodiesel Production," https://farm-energy.extension.org/reactors-for-biodiesel-production/, 5 pages, (Apr. 3, 2019; retrieved Apr. 9, 2024).
Handa et al., "A highly stereoselective pinacolization of aromatic and a, ß—unsaturated aldehydes mediated by titanium(III)-magnesium(II) complex," Tetrahedron Letters No. 28, 5717-5718, (1987).
Hoydonckx et al., "Furfural and Derivatives," Ullman's Encyclopedia of Industrial Chemistry, Wiley-VCH, 16:285-313, (2000).
Kinlen et al., "Mechanistic studies of the electrohydrodimerization of acrylonitrile," Journal of Electroanalytical Chemistry and Interfacial Electrochemistry, 304(1-2): 133- 151, (Apr. 10, 1991).
Li et al., "Pinacol coupling of aromatic aldehydes and ketones by TiCL4-MG under ultrasound irradiation," Ultrasonics Sonochemistry, 12:349-352, (2005).
Li et al., "MeOH or H2O as efficient additive to switch the reactivity of allylSmBr towards carbonyl compounds," Tetrahedon Letters, 58:1250-1253, (2017).
Liu et al., "Pinacolization of aromatic aldehydes using Zn/mont morillonite ZnC1 and ultrasound," Journal of Hebei University of Science and Technology, 26(1):25-27, 35, (Mar. 2005).
Raffa et al., "First examples of gold nanoparticles catalyzed silane alcoholysis and silylative pinacol coupling of carbonyl compounds," Tetrahedron Letters, 49(12):3221- 3224, (2008).
Scifinder, Search Results for "synthesis of 116204-42-3", 8 pages, (retrieved Apr. 7, 2020).
Shi et al., "Novel and efficient Ni-mediated pinacol coupling of carbonyl compounds," Science Direct, 60(12):2851-2855, (2004).
Takai, "Reductive Coupling Reactions Promoted by Low-valent Early Transition Metals and Lanthanoids," Comprehensive Organometallic Chemistry III, 39-73, (2007).

(56) References Cited

OTHER PUBLICATIONS

Wang et al., "Magnesium-Induced Pinacol Coupling of Aromatic Aldehydes and Ketones Under Ultrasound Irradiation," Synthetic Communications®, 35:1419-1424, (2005).
Zhang et al., "Efficient Production of Furfural from Corncob by an Integrated Mineral-Organic-Lewis Acid Catalytic Process," BioResources, 12(2):2965-2981, (2017).

* cited by examiner

REDUCTIVE DIMERIZATION OF FURFURAL VIA A CONTINUOUS PROCESS

CROSS-REFERENCE TO RELATED APPLICATIONS

This application claims the benefit of and priority to U.S. Provisional Patent Application No. 63/082,681, filed on Sep. 24, 2020, which is incorporated by reference herein in its entirety for all purposes.

FIELD OF THE INVENTION

The presently disclosed subject matter relates generally to methods for the continuous preparation of 1,2-di(furan-2-yl)ethane-1,2-diol from furan-2-carbaldehyde.

BACKGROUND

A significant portion of the chemical industry is dependent on fossil raw materials. Even as renewable sources of energy increase, the reliance of crude oil feedstock for industrial and consumer chemicals has not abated, compounded by an increasing share of heavier and non-conventional sources of this oil. Indeed, the surging demand for chemicals and precursors for plastics, especially in developing economies such as India or China, will in the next decades lead to a need for more suitable feedstock in industrial chemistry. In view of this problem, renewable raw materials are a promising feedstock alternative for the chemical industry. Biomass and waste oil generated 71.4 billion kilowatt hours of electricity in 2016, or 2% of total generation in the United States (U.S. Energy Information Administration, Power Plant Operations Report). Nature produces about 170 billion tons per annum of biomass by photosynthesis, of which only 3-4% is utilized by mankind. Carbohydrates assume the largest component at 75%. (A. Corma. et al., *Chem. Rev.* 2007, 107, 241-2502). They occur mostly in the form of polysaccharides, which are composed of $C_5$- or $C_6$-monosaccharides. The polysaccharides hemicellulose ($C_5$) and cellulose ($C_6$) form, by incorporation of the phenolic biopolymer lignin, lignocellulose, which is the structural framework of all woody plants. It is obtained in large quantities as a waste product in agriculture and forestry. Furfural is a chemical intermediate produced industrially exclusively from such biological waste (H. E. Hoydonckx et al., *Ullmann's Encyclopedia of Industrial Chemistry* WILEY-VCH (2000). It is at present the only unsaturated bulk chemical produced from carbohydrates (P. Gallezot, *Chem. Soc. Rev.* 2012, 41, 1538-1558).

Furfural was isolated for the first time in 1831 by the German Chemist Wolfgang Dobereiner as a by-product in the synthesis of formic acid when he treated carbohydrates with sulfuric acid and $MnO_2$ (J. W. Döbereiner, Berichte der deutschen chemischen Gesellschaft 1832, 3, 141-146). Currently, biological wastes obtained, for example, in the growing of sugar and maize, serve as starting materials for furfural production. These materials contain hemicellulose, which is present as a constituent of lignocellulose in the cell walls of most plants. Hemicellulose is a mixture of polysaccharides, which have a variable composition and contain mainly pentoses (simple sugars having five carbon atoms) as monomers. Treatment with hot sulphuric acid results in hydrolysis of hemicellulose and liberation of the monosaccharides. Under these reaction conditions, dehydration of the pentoses to furfural occurs as a subsequent reaction. Worldwide production of furfural is estimated to be approximately 300,000 metric tons/year (Takkellapati S, Li T, Gonzalez MA *Clean Technologies and Environmental Policy.* 2018 Sep., 20(7):1615-1630). Furfural can be converted into a variety of solvents, polymers, fuels and other useful chemicals by a range of catalytic reductions. Hydrogenation of furfural provides furfuryl alcohol, which is used to produce furan resins. Furan resins are exploited in thermoset polymer matrix composites, cements, adhesives, casting resins, and coatings. Further hydrogenation of furfuryl alcohol leads to tetrahydrofurfuryl alcohol, which is used as a solvent in agricultural formulations. Reductive coupling of furfural produces a pinacol (1,2-di(furan-2-yl)ethane-1,2-diol), which can provide a highly pure biofuel additive or fuel precursor.

While 1,2-di(furan-2-yl)ethane-1,2-diol offers great potential as a biofuel material, its production is quite limited. The reductive dimerization of aldehydes or ketones to synthesize 1,2-diols conventionally proceeds by batch reactions. These batch reactions are often slow, generate a great deal of waste, and feature challenges with chemoselectivity and stereoselectivity. The subject matter described herein addresses an unmet need for a sustainable process.

BRIEF SUMMARY

In one aspect, the presently disclosed subject matter is directed to a method for continuously preparing 1,2-di(furan-2-yl)ethane-1,2-diol from furan-2-carbaldehyde.

In another aspect, the presently disclosed subject matter is directed to a method for the continuous preparation of 1,2-di(furan-2-yl)ethane-1,2-diol from furan-2-carbaldehyde, wherein said preparation proceeds in a continuous flow system.

In another aspect, the presently disclosed subject matter is directed to an electrochemical process comprising a static mixer.

In another aspect, the presently disclosed subject matter is directed to an electrochemical continuous flow system for reductively dimerizing furan-2-carbaldehyde to prepare 1,2-di(furan-2-ypethane-1,2-diol.

These and other aspects are described fully herein.

DETAILED DESCRIPTION

The subject matter described herein relates to methods for the continuous preparation of 1,2-di(furan-2-ypethane-1,2- diol from furan-2-carbaldehyde. What is needed in the art are effective, low-cost, and environmentally preferred methods for the reductive dimerization of furfural to 1,2-di(furan-2-yl)ethane-1,2-diol. The continuous preparative methods can proceed both chemically and electrochemically and offer a variety of advantages compared to conventional batch reactions.

Figure 1:
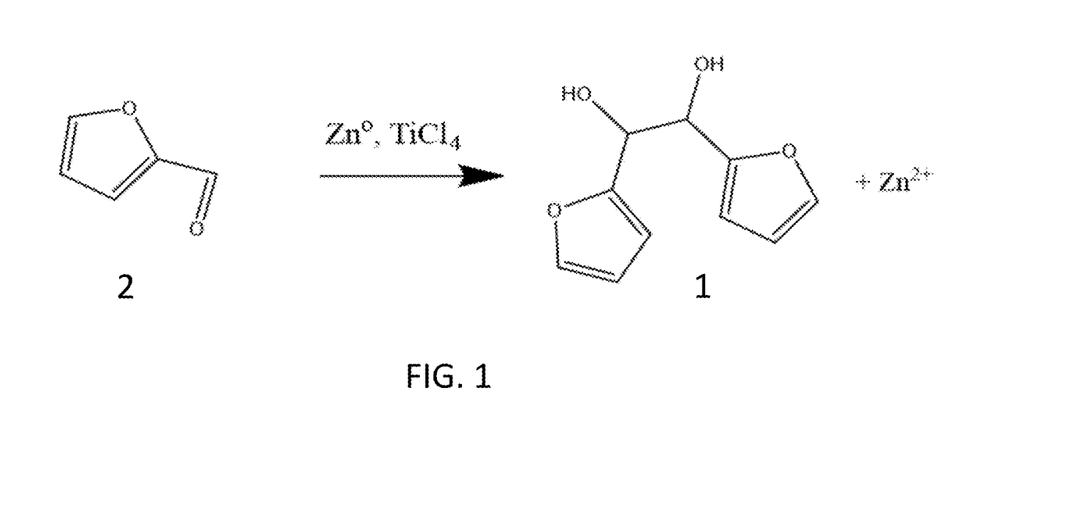
FIG. 1 shows a general reaction scheme for furfural pinacol chemical coupling.

Traditionally, coupling reactions of aldehydes or ketones to 1,2-diols proceeds with metals such as magnesium, zinc, or aluminum (K. Takai, *Comprehensive Organometallic Chemistry III* 2007: 39-73; Elseview Ltd.). FIG. 1 shows a general reaction scheme for the pinacol coupling of furfural to yield the 1,2-diol. Although the coupling reaction of carbonyl-containing compounds proceeds in the presence of strong reducing agents, such as magnesium, maintaining control over the stereochemistry and stereoselectivity of the resulting product has presented several challenges by traditional batch processes. Low-valent, early transition metals (i.e. Ti) or lanthanide metals (i.e. Sm) bearing electron-donating ligands are often employed in these reactions with main-group metals as a means to better control the stereoselectivity.

The stereoselectivity problems encountered in the batch reactions are particularly problematic when it comes to reaction scale-up. In the conventional reductive dimerization batch reactions, volatile organic solvents are required, such as THF, dichloromethane, toluene, or acetonitrile. These non-aqueous solvents are undesirable and become even more problematic during scale-up. For example, the metal powders must be dispersed in the medium using high speed mixing, which increases in difficulty as the reaction vessel increases in size. Furthermore, the low temperature (~0° C.) required for the reaction to proceed is complicated to maintain during the full reaction progression. In addition to this, batch reactions typically require a large environmental footprint, through chemical waste, greenhouse gas emissions, and energy use.

Figure 2:
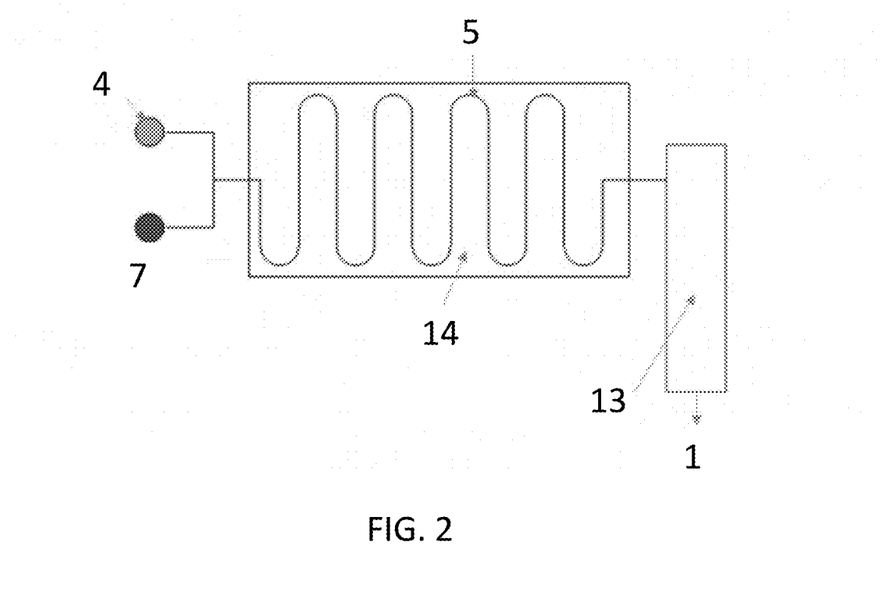
FIG. 2 shows a schematic of a continuous flow chemistry reactor described herein.

The continuous flow reactions described herein address the problems encountered in batch reactions in the reductive dimerization of furan-2-carbaldehyde to prepare 1,2-di(furan-2-yl)ethane-1,2-diol. As described herein, the continuous flow reactor allows for precise control of the reactant addition (furfural), catalysts (i.e. Ti salts), and pH. By employing a coolant in the reactor setup, the method further allows for precise control of temperature, which allows for the minimization of potential byproducts, thereby enhancing yield. Application of a static mixer in the reaction zone provides efficient mixing of the reactants. Additionally, designing the static mixer with a metal deposited on its surfaces eliminates the need to add metal powder to the reaction mixture, itself. This can lead to significant cost savings, as the metal on the mixer can be recycled during the continuous flow reaction. The closed system of the continuous flow reactor also imparts greater safety when employing volatile organic solvents. These advantages provide higher yields for chemoselectivity and selectivity of the pinacol. Additionally, the continuous flow reactions are much more scalable than batch reactions and provide an overall smaller environmental footprint. A proposed chemical, continuous flow reactor is shown in FIG. 2.

The continuous flow systems described herein are able to balance the flow of reactants and prevent side reactions. This is achieved through the combination of effective mixing, pH control, and temperature control. The goal of the reaction is to reduce the aldehyde and cause dimerization, but not the production of furfural alcohols. The reaction is a second order reaction. As described herein, the continuous process can proceed chemically or electrochemically.

Figure 3:
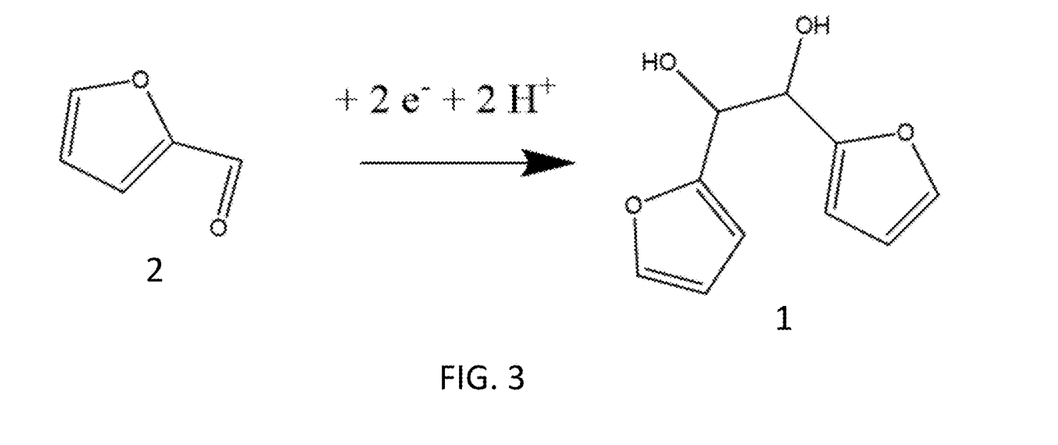
FIG. 3 shows a general reaction scheme for furfural pinacol electrochemical coupling.

In comparison to the continuous flow chemical conversion, electrochemical conversion uses an electrode (cathode) to supply electrons to the aldehyde to then be reduced. As such, zinc (or another metal) is not required in the electrochemical continuous flow process. The electrochemical approach also produces no metal ions that need to be removed downstream by ion exchange. The configuration results in high current efficiency, yield, and product purity. A schematic showing the electrochemical reaction conversion is provided in FIG. 3. Without wishing to be bound by theory, it is understood that the reaction proceeds by the formation of a hydrophobic reaction layer adjacent to the cathode surface. The addition of a quaternary ammonium salt helps suppress hydrogen evolution during the reaction. Such electrohydrodimerization does not require a power supply, therefore resulting in decreased power consumption.

The methods described herein enable the preparation of 1,2-di(furan-2-yl)ethane-1,2-diol in high chemoselectivity and stereoselectivity. The continuous flow methods offer enhanced chemoselectivity of the final pinacol product compared to a batch method through improved control of experimental variables such as pH, reagents, and temperature. The stereochemistry of the product can be further focused by adjusting these variables.

Diarylethane diols, such as 1,2-di(furan-2-yl)ethane-1,2-diol, are often used as intermediates for the construction of biologically important skeletons of natural products, and as asymmetric ligands for catalytic asymmetric reactions. These diarylethane diols also hold many applications as monomers for the preparation of polyester and polyurethane polymers. These polymers can be used as liquid crystals, as chiral separating agents for enantiomers, and in medical applications (see WO2013135869A1). As such, the 1,2-di(furan-2-yl)ethane-1,2-diol produced herein can be used in a number of different applications.

The presently disclosed subject matter will now be described more fully hereinafter. However, many modifications and other examples of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to specific examples disclosed and that modifications and other examples are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literatures, patents, and similar materials differs from or contradicts this application, including but not limited to defined terms, term usage, described techniques, or the like, this application controls.

I. Definitions

As used herein, "and/or" refers to and encompasses any and all possible combinations of one or more of the associated listed items, as well as the lack of combinations when interpreted in the alternative ("or").

As used herein, the term "about," when referring to a measurable value such as an amount of a compound or agent of the current subject matter, dose, time, temperature, and the like, is meant to encompass variations of ±20%, ±10%, ±5%, ±1%, ±0.5%, or even ±0.1% of the specified amount.

The terms "approximately," "about," "essentially," and "substantially" as used herein represent an amount close to the stated amount that still performs a desired function or achieves a desired result. For example, in some examples, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic.

As used herein, conditional language used herein, such as, among others, "can," "could," "might," "may," "e.g.," and the like, unless specifically stated otherwise or otherwise understood within the context as used, is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

As used herein, "batch method" or "batch process" refers to a process in which a series of operations are carried out over a period of time on a separate, identifiable chemical to produce a product.

As used herein, "continuous flow method" or "continuous process" refers to moving one work unit at a time between each step of the process, with no breaks in time, sequence, substance, or extent.

As used herein, "reaction zone" refers to the reactor in the continuous flow system, which, in examples, comprises the reactants, catalysts, static mixer, and coolant. The reaction zone is the location in the continuous flow system where the reaction proceeds.

II. Chemical Continuous Flow System

The subject matter disclosed herein is directed to a method for continuously preparing 1,2-di(furan-2-ypethane-1,2-diol from furan-2-carbaldehyde In certain examples of the continuous preparation methods described herein, the methods proceed in a continuous flow system. In certain examples, the continuous flow system is as depicted in FIG. 2.

In certain examples, the method comprises:
introducing a first reactant stream comprising the furan-2-carbaldehyde into a reactor column comprising a metal;
introducing a second reactant stream comprising a catalyst into the reactor column;
contacting the first reactant stream with the second reactant stream to form a mixture; and passing the mixture through the column to produce the 1,2-di(furan-2-yl)ethane-1,2-diol;
wherein the method proceeds in the presence of a solvent.

In certain examples of the above method, the continuous flow system comprises stainless steel tubing. Nonlimiting examples of the stainless steel employed in the system include 304 (contains 18% chromium and 8% nickel) or 316 (contains 16% chromium, 10% nickel and 2% molybdenum). In certain examples of the above method, the continuous flow system comprises one or more plastic(s). Nonlimiting examples of the plastic employed in the system include TEFLON or polypropylene.

In certain examples of the above method, the total volume of the reactor employed in the continuous flow system is between 0.5 and 5 liters. In certain examples, the total volume of the reactor is between 1 and 3 liters, 2 and 4 liters, 0.75 and 4.5 liters, 1.5 and 3.5 liters, 2.5 and 4.75 liters, or 0.75 and 2 liters.

In certain examples of the above method, the inner diameters of the tubing employed in the continuous flow system is from 1 mm to 5 cm. In certain examples, the inner diameters of the tubing employed in the continuous flow system is from 1 cm to 5 cm, 1 mm to 5 mm, 1 mm to 7 mm, 1 mm to 3 cm, or 2 mm to 1.5 cm. In examples, the inner diameter of the tubing is dependent on the overall size of the continuous flow setup.

In certain examples of the above method, the solvent can be mixed with the first and/or second reactant stream and introduced to the reactor column with the reactants. In certain examples, the solvent can be introduced to the reactor column independently of the reactant(s). In certain examples of the above method, the reactor column comprising a metal comprises a packed bed comprising the metal. In certain examples, the bed comprises porous catalytic particles or beads, or porous monoliths embedded with the metal. In certain examples, the metal reactant (Zn) is converted to $Zn^{2+}$ and the reactor can be sacrificial. In certain examples, the flow-through reactor bed comprising Zn is porous.

In certain examples, the metal reactant, such as Zn, Cu, Mg, Li, or Mn, is converted to its metal ion and the reactor column is essentially sacrificial. In certain examples, the tubing comprising the reactor column is zinc-plated steel.

In certain examples of the above method, the reactor column comprising a metal comprises a static mixer wherein the metal is deposited on surfaces of the static mixer. In certain examples, the metal is selected from the group consisting of Cu, Zn, Mn, Mg, Li, Al, Ni, Pd, Rh, Ru, Co, and Pt. In certain examples, the metal is Zn. In certain examples, the metal is deposited on surfaces of the static mixer by electroplating or cold spraying. One benefit of the metal-coated static mixer is that it can provide a continuous supply of metal without needing to be replaced during the reaction.

In certain examples of the above method, the solvent is selected from the group consisting of tetrahydrofuran, dichloromethane, toluene, acetonitrile, diethyl ether, methanol, and N,N-dimethylformamide.

In certain examples of the above method, the catalyst is a transition metal salt or a rare earth metal salt. In certain examples, wherein the catalyst is a transition metal salt, the transition metal salt is selected from the group consisting of a titanium salt, zirconium salt, and hafnium salt. In certain examples, the transition metal salt is a titanium salt. In certain examples, the titanium salt is selected from the group consisting of $TiCl_4$, $TiBr_4$, $TiI_4$, di(cyclopentadienyl)titanium(IV) dichloride, and $TiCl_3$. In certain examples, the titanium salt is $TiCl_4$.

In certain examples of the above method, wherein the catalyst is a rare earth metal salt, the rare earth metal salt is a lanthanide salt. In certain examples, wherein the catalyst is a rare earth metal salt, the rare earth metal salt is a samarium salt, cerium salt, praseodymium salt, or neodymium salt. In certain examples, the rare earth metal salt is a samarium salt.

In certain examples of the above method, the method further comprises contacting the mixture with an ion exchange material. In certain examples, the ion exchange material is a cationic or anionic exchange material. As such, in certain examples, the metal ion formed may be removed from the product using a cation exchange resin. Non-limiting examples of cationic exchange resins include monovinylidene aromatic crosslinked polymer, or (meth) acrylic acid ester-based crosslinked polymer. In certain examples, the ion exchange material is polystyrene sulphonate. In certain examples, the ion exchange material is crosslinked.

Non-limiting examples of resins include AMBERLITE IRC 747, AMBERSEP 400 $SO_4$, AMBERSEP 4400 $HCO_3$, AMBERSEP 748 UPS, AMBERSEP 920 UXL $C_1$, AMBERSEP 920U $C_1$, AMBERSEP 920U$HCSO_4$, AMBERSEP GT74, DOWEX™ 21K 16-20, DOWEX 21K XLT, DOWEX Mac-3, DOWEX RPU, XUS-43578, XUS-43600, XUS-43604, XUS-43605, and XZ-91419, all available from The Dow Chemical Company, Midland, Mich. In certain examples, the exchange resin is AMBERLITE IR120, AMBERJET1500, AMBERLYST 15 (macro reticular polystyrene based ion exchange resin with strongly acidic sulfonic group), or AMBERSEP 200.

In certain examples, a post-reaction purification step can be used to purify the pinacol. In certain examples, the post-reaction purification step is vacuum distillation. In certain examples, the post-reaction purification step is centrifugation. In certain examples, the method further comprises distilling the mixture, for example, by vacuum distillation.

In certain examples, the method further comprises filtering the mixture. In certain examples, the method further comprises centrifuging the mixture.

In certain examples of the above method, the mixture maintains a pH of about 3. In certain examples of the above method, the mixture maintains a pH of about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0. In certain examples, acid or base can be added to the reaction mixture to adjust its pH. In certain examples, acid or base can be added with either the furan-2-carbaldehyde in the first reactant stream or with the catalyst in the second reactant stream, or independently. In certain examples, the acid or base is anhydrous.

In certain examples of the above method, the method proceeds at a temperature of about −30° C. to 150° C., −20° C. to about 100° C., −10° C. to about 70° C., −5° C. to about 50° C., −5° C. to about 30° C., −2° C. to about 20° C., 0° C. to about 15° C., −5° C. to about 5° C., or about −2° C. to about 2° C. In certain examples, the method proceeds at a temperature of about 0° C.

In certain examples of the above method, the reactor column has a pressure of about 1, 2, 3, 4, 5, 6, 7, 8, 9, 10, 11, 12, 13, 14, 15, 16, 17, 18, 19, or 20 atm.

In certain examples of the above method, the first reactant stream comprising the furan-2-carbaldehyde has a flow rate of about 0.01 L/min to about 100 L/min. In certain examples, the first reactant stream comprising the furan-2-carbaldehyde has a flow rate of about 0.01 L/min, 0.10 L/min, 1.0 L/min, 5.0 L/min, 10.0 L/min, 20.0 L/min, 30.0 L/min, 40.0 L/min, 50.0 L/min, 60.0 L/min, 70.0 L/min, 80.0 L/min, 90.0 L/min, or 100 L/min.

In certain examples of the above method, the second reactant stream comprising said catalyst has a flow rate of about 0.01 L/min, 0.10 L/min, 1.0 L/min, 5.0 L/min, 10.0 L/min, 20.0 L/min, 30.0 L/min, 40.0 L/min, 50.0 L/min, 60.0 L/min, 70.0 L/min, 80.0 L/min, 90.0 L/min, or 100 L/min.

In certain examples of the above method, the solvent is present in about 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0 volumes.

In certain examples of the above method, the raw materials can be de-aerated or blanketed with argon or nitrogen gas in the feed vessels prior to use.

In certain examples of the above method, the method proceeds for about 1 min, 2 min, 3 min, 5 min, 10 min, 20 min, 30 min, 40 min, 50 min, 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 20 hrs, 24 hrs, 25 hrs, 26 hrs, 27 hrs, 28 hrs, 29 hrs, 30 hrs, 36 hrs, 40 hrs, 48 hrs, 54 hrs, 60 hrs, 65 hrs, 68 hrs, 72 hrs, 80 hrs, 85 hrs, 90 hrs, 96 hrs, or 100 hrs.

The ability to control the temperature, time, pH, and reactant streams in the continuous flow system described herein enables the production of 1,2-di(furan-2-yl)ethane-1,2-diol in greater purity, chemoselectivity, stereoselectivity, and yield than batch methods.

In certain examples of the above method, the method produces 1,2-di(furan-2-yl)ethane-1,2-diol in higher chemoselectivity than a batch method. In certain examples, the method produces 1,2-di(furan-2-yl)ethane-1,2-diol in greater chemoselectivity than a furfural alcohol, for example. In certain examples of the above method, the method produces 1,2-di(furan-2-yl)ethane-1,2-diol in 10%, 20%, 30%, 40%, 50%, 60%, 70%, 75%, 80%, 85%, 86%, 87%, 88%, 89%, 90%, 91%, 92%, 93%, 94%, 95%, 96%, 97%, 98%, or 99% greater chemoselectivity than a batch method. Non-liming methods to determine the chemoselectivity of the product include NMR, mass spectrometry, or gas or liquid chromatography.

In certain examples of the above method, the method produces 1,2-di(furan-2-yl)ethane-1,2-diol in higher purity than a batch method. In certain examples of the above method, the method produces 1,2-di(furan-2-yl)ethane-1,2-diol in 85%, 86%, 87%, 88%, 89%, 90%, 91%, 92%, 93%, 94%, 95%, 96%, 97%, 98%, 99%, or 100% purity. In certain examples of the above method, the method produces 1,2-di(furan-2-yl)ethane-1,2-diol in 10%, 20%, 30%, 40%, 50%, 60%, 70%, 80%, 90%, or 95% greater purity than a batch method. Non-limiting methods to determine the purity of the product include melting point, gas or liquid chromatography, mass spectroscopy, capillary electrophoresis, or optical rotation.

In certain examples of the above method, the method produces 1,2-di(furan-2-yl)ethane-1,2-diol in higher yield than a batch method. In certain examples of the above method, the method produces 1,2-di(furan-2-yl)ethane-1,2-diol in 40%, 50%, 60%, 70%, 80%, 90%, 91%, 92%, 93%, 94%, 95%, 96%, 97%, 98%, 99%, or 100% yield. In certain examples of the above method, the method produces 1,2-di(furan-2-yl)ethane-1,2-diol in 30%, 40%, 50%, 60%, 70%, 75%, 80%, 85%, 90%, 95%, 96%, 97%, 98%, or 99% greater than yield than a batch method. The percent yield can be determined by the following equation: % yield=(actual yield/theoretical yield)×100.

In an example of the method above, the continuous flow system comprises a reactor comprising stainless steel tubing of type 304; the total volume of the reactor is 3 L; the inner diameter of the tubing employed in the system is about 5 mm; the solvent is mixed with the first reactant stream with the furfural; the solvent is toluene; the first reactant stream has a flow rate of about 1.0 L/min; the second reactant stream contains the catalyst, which is $TiCl_4$; the second reactant stream has a flow rate of about 1.0 L/min; the reactor comprises a static mixer where a metal is deposited on surfaces of said mixer; the metal is Zn; the reaction proceeds at a temperature of about 0° C.; the reaction proceeds at a pressure of about 1 atm; the method further comprises contacting the mixture with an ion exchange material; the ion exchange material is a cationic exchange material; the cationic exchange material is a monovinylidene aromatic crosslinked polymer; and, the method proceeds for about 6 hrs.

III. Chemical Continuous Flow System Assembly

In certain examples, the subject matter disclosed herein is directed to a continuous flow system for preparing 1,2-di(furan-2-yl)ethane-1,2-diol from furan-2-carbaldehyde.

In certain examples of the continuous flow system, the system comprises: a first reactant stream comprising the furan-2-carbaldehyde; a second reactant stream comprising a catalyst; a solvent; and a reactor column comprising a metal.

In certain examples of the continuous flow system, the system further comprises a coolant. In certain examples, the coolant comprises ethylene or propylene glycol mixtures in water. In certain examples, the coolant is antifreeze.

In certain examples of the continuous flow system, wherein the reactor column comprising a metal comprises a static mixer, the metal is deposited on surfaces of the static mixer. In certain examples, the metal is Zn. In certain examples, the metal is deposited on surfaces of the static mixer by electroplating or cold spraying.

In certain examples of the continuous flow system, the reactor column comprising a metal comprises a packed bed comprising the metal.

In certain examples of the continuous flow system, the system further comprises a column comprising an ion exchange material.

In certain examples of the above continuous flow system, the system comprises stainless steel tubing. Nonlimiting examples of the stainless steel employed in the system include 304 (contains 18% chromium and 8% nickel) or 316 (contains 16% chromium, 10% nickel and 2% molybdenum). In certain examples of the above continuous flow system, the system comprises one or more plastic(s). Nonlimiting examples of the plastic employed in the system include TEFLON or polypropylene. In certain examples, the tubing comprising the reactor column is zinc-plated steel.

In certain examples of the above continuous flow system, the total volume of the reactor employed in the system is between 0.5 and 5 liters. In certain examples, the total volume of the reactor is between 1 and 3 liters, 2 and 4 liters, 0.75 and 4.5 liters, 1.5 and 3.5 liters, 2.5 and 4.75 liters, or 0.75 and 2 liters.

In certain examples of the above continuous flow system, the inner diameters of the tubing employed in the system is from 1 mm to 5 cm. In certain examples, the inner diameters of the tubing employed in the continuous flow system is from 1 cm to 5 cm, 1 mm to 5 mm, 1 mm to 7 mm, 1 mm to 3 cm, or 2 mm to 1.5 cm.

In certain examples of the continuous flow system, the solvent can be mixed with the first and/or second reactant stream and introduced to the reactor column with the reactants. In certain examples, the solvent can be introduced to the reactor column independently of the reactant(s).

IV. Electrochemical Continuous Flow System

In certain examples, the subject matter described herein is directed to a method for continuously preparing 1,2-di(furan-2-yl)ethane-1,2-diol from furan-2-carbaldehyde, wherein the method proceeds by an electrochemical process. The electrochemical process proceeds by means of a diffusion layer that is generated on the cathode. As such, the various elements that contribute to the configuration of the electrochemical continuous flow system must together enable the generation of the diffusion layer.

In certain examples of the above method, the electrochemical process comprises reductively dimerizing furan-2-carbaldehyde to prepare 1,2-di(furan-2-ypethane-1,2-diol by passing a direct electrical current through an electrolytic cell having an anode and a cathode in contact with an electrolytic medium.

In certain examples of the above method, the electrolytic medium comprises an initial electrolysis medium comprising furan-2-carbaldehyde, water, and at least one salt. In certain examples, the at least one salt is selected from the group consisting of sodium, potassium, lithium, and ammonium. As surface-active substances, there may be used quaternary ammonium salts or pyridinium salts, such as acidic bis-tetraethyl-ammonium phosphate, penta-tetraethyl-ammonium tripolyphosphate, acidic bis-methylpyridinum phosphate, tetrabutylammoniumfluoroborate (TBA), dodecylethyldimethylammonium bromide (DEDMA), tetrabutylammonium phosphate, bisdibutylethylammonium-hexane-1,6 dihydroxide (BISQA), or the like.

The concentration of these surface-active substances in the aqueous electrolytic solution may vary from 0.05 to 5 percent by weight, preferably from 0.01 to 2 percent.

The amount of salt should be sufficient for the formation and maintenance of a hydrophobic layer on the electrode for the duration of the reaction. The hydrophobic layer drives the increased solubility of the furfural. A concentration of furfural of at least 70%, preferably at least or about 95% leads to dimerization, which concentrates on the hydrophobic layer on the electrode. This improves the conversion efficiency to the dimer (pinacol), as opposed to forming an alcohol. In certain examples of the above method, an amount of base or acid is added to the medium to maintain a pH of about 2 to about 5. In certain examples, an amount of base or acid is added to said medium to maintain a pH of about 3. In certain examples, an amount of base or acid is added to said medium to maintain a pH of about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0.

In the course of the reaction, a mixture of the furfural and of the initial aqueous electrolytic solution is circulated through the apparatus, the volumetric ratio between the aqueous phase and the furfural phase being maintained within the limits of 1:1 and 50:1. In certain examples, the volumetric ratio between the aqueous phase and the furfural phase being maintained within the limits of 1:1 and 20:1, 1:1 and 15:1, 1:1 and 10:1, or 1:1 and 5:1.

Figure 7:
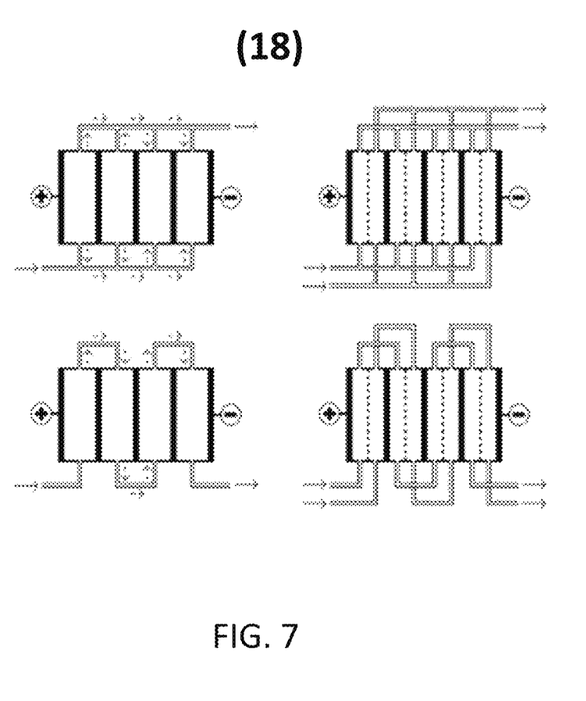
FIG. 7 shows a schematic of an exemplary bipolar configuration described herein, which allows for multiple flow cells in parallel.
Figure 8:
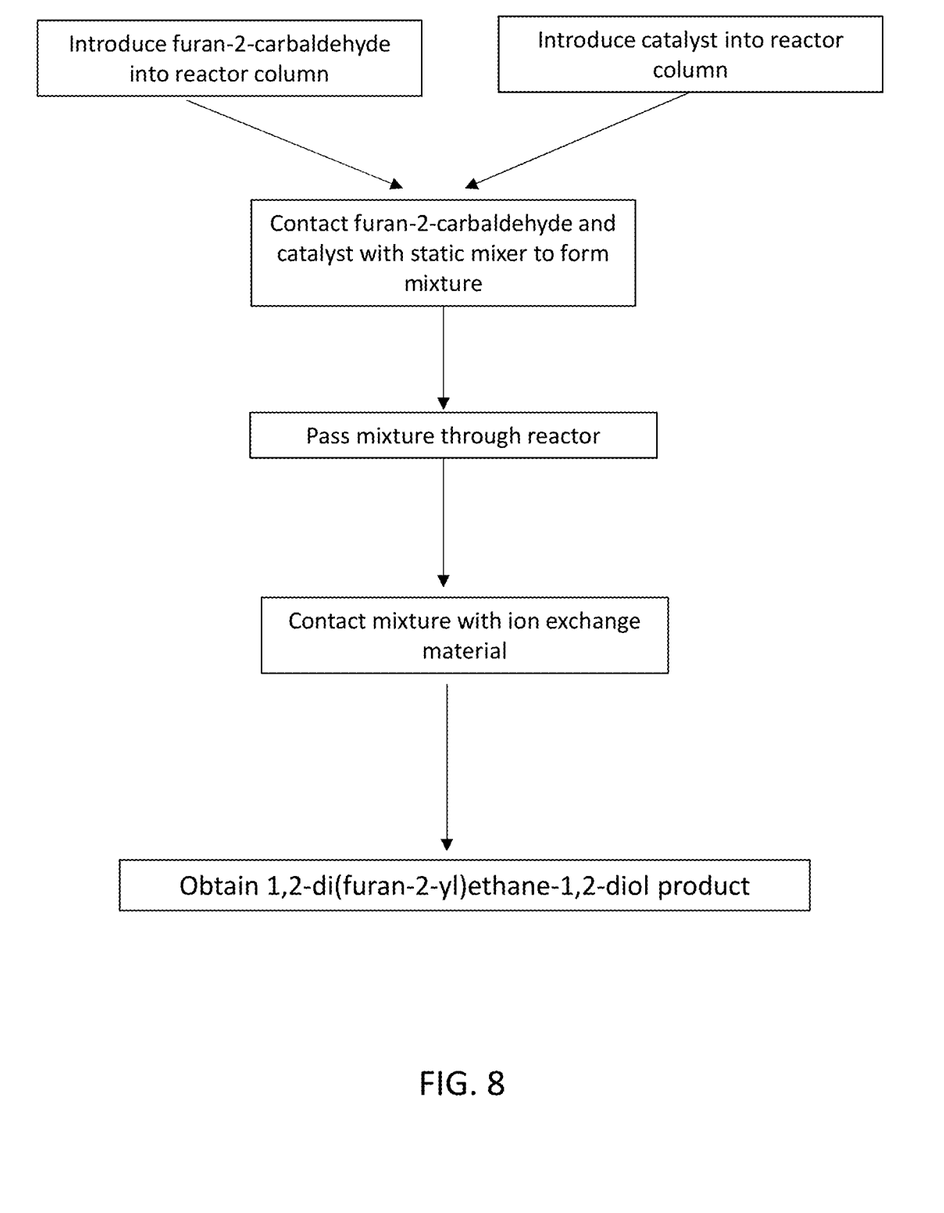
FIG. 8 shows a process flow chart for preparing 1,2-di(furan-2-yl)ethane-1,2-diol via a chemical continuous flow method.
Figure 9:
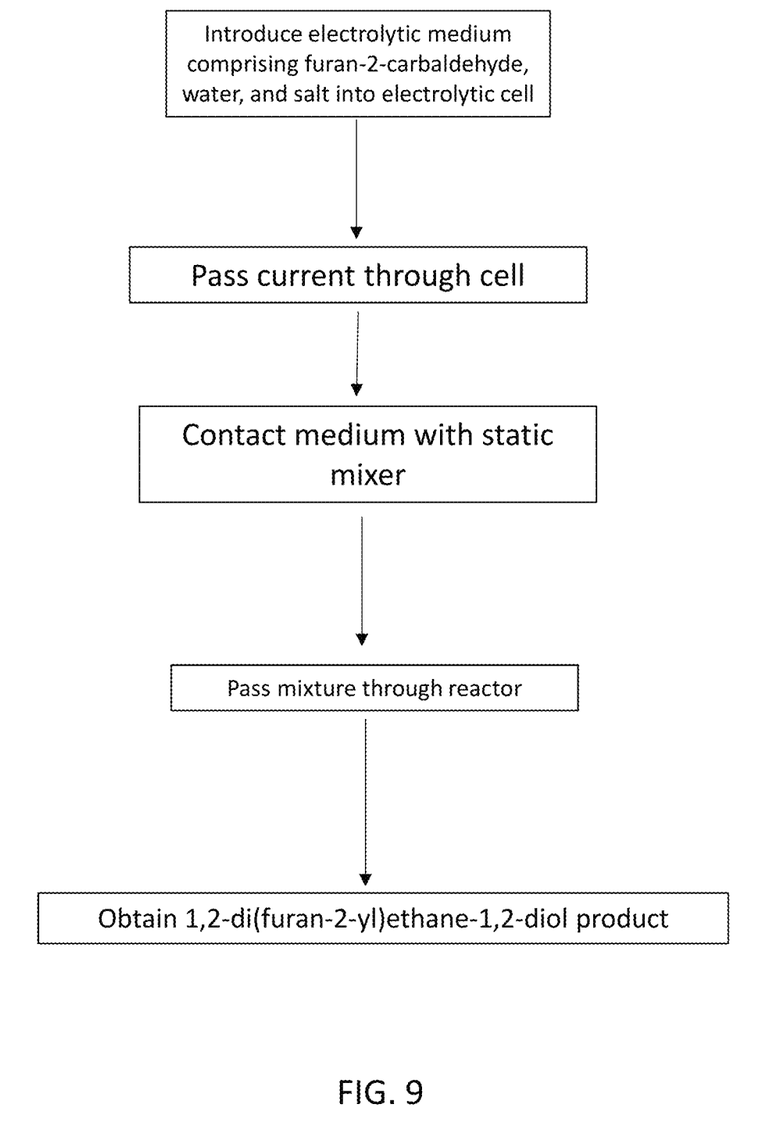
FIG. 9 shows a process flow chart for preparing 1,2-di(furan-2-yl)ethane-1,2-diol via an electrochemical continuous flow method.

In certain examples of the above method, the method further comprises a static mixer. The static mixer can provide efficient mixing, intimate contact with the electrode surface, and electrical isolation of the anode from the cathode. In certain examples, a parallel plate reactor stackup can be implemented (FIG. 7).

In certain examples of the above method, the electrochemical process proceeds at a temperature of about −30° C. to 150° C., −20° C. to about 100° C., −10° C. to about 70° C., −5° C. to about 50° C., −5° C. to about 30° C., −2° C. to about 20° C., 0° C. to about 15° C., −5° C. to about 5° C., or about −2° C. to about 2° C. In certain examples, the method proceeds at a temperature of about 0° C. In certain examples, a coolant is used to maintain the temperature in the electrochemical process.

In certain examples of the above method, the velocity of circulation of the mixture is between 0.1 and 100 m/sec. In certain examples, the velocity of circulation of the mixture is between 0.1 and 75 m/sec, 0.1 and 50 m/sec, 0.1 and 25 m/sec, 0.1 and 10 m/sec, and 0.1 and 50 m/sec. The selection of the mixer velocity can help minimize cavitation and vaporization, which can decrease the efficiency of the process. The selected velocity is dependent on certain factors, such as viscosity, vapor pressure of the reaction, as well as the concentration.

Figure 5:
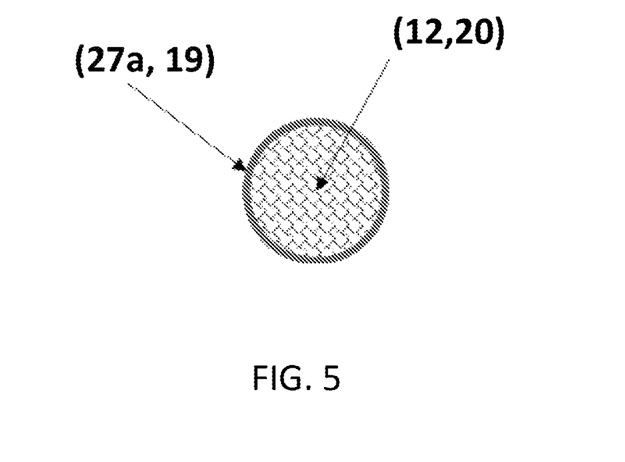
FIG. 5 shows a cross-section of a continuous flow electrochemical annular reactor described herein.
Figure 6:
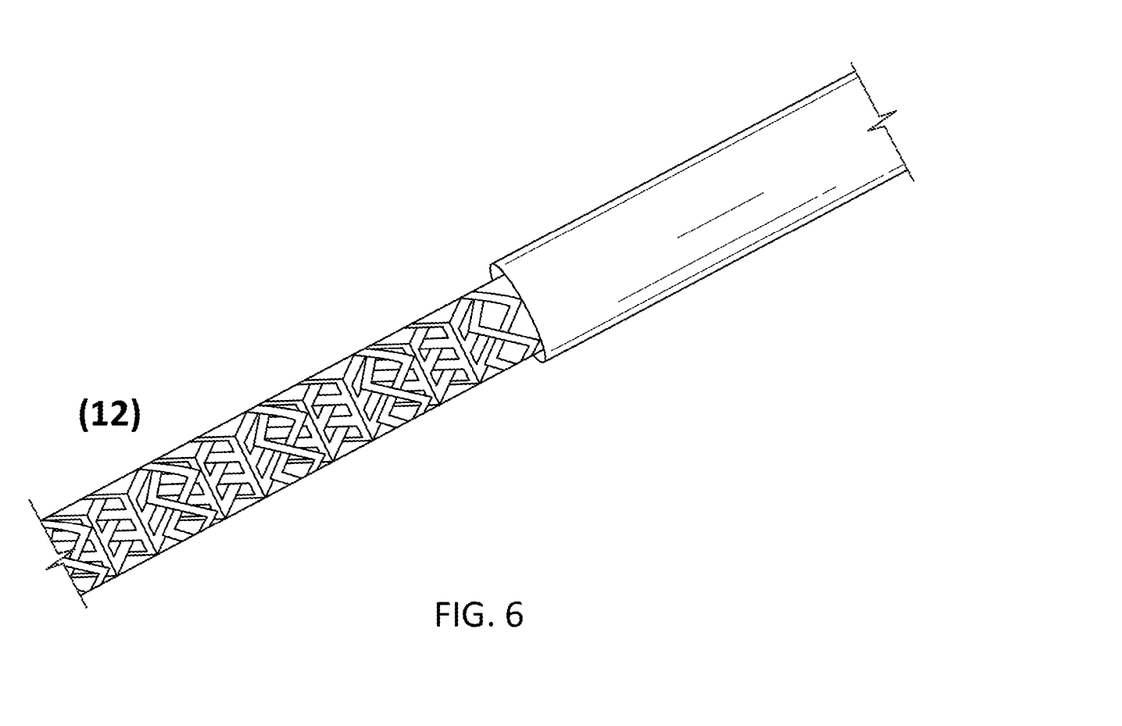
FIG. 6 shows a photograph of the outer tubing wall of an exemplary static mixer described herein.

In certain examples of the above method, the cathode and anode each comprise at least one of lithium, sodium, potassium, rubidium, cesium, francium, beryllium, magnesium, calcium, strontium, barium, radium, boron, aluminum, gallium, indium, thallium, tin, lead, flerovium, bismuth, antimony, tellurium, polonium, scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, copernicium, samarium, neodymium, ytterbium, an alkali metal fluoride, an alkaline-earth metal fluoride, an alkali metal chloride, an alkaline-earth metal chloride, an alkali metal oxide, an alkaline-earth metal oxide, carbon steel, a metal carbonate, a metal acetate, carbon nanowire, carbon nanosheet, carbon nanorod, carbon nanotube, graphite, or mixtures or alloys thereof. In certain examples, the static mixer is the cathode and the annular reaction wall is the anode (FIG. 5). In certain examples, the anode is selected from the group consisting of steel, carbon, and platinum and the cathode is selected from the group consisting of zinc and copper.

In certain examples of the above method, the current density is 1-30 amperes/dm$^2$ and the voltage is between about 4 and 10 volts or about 4 and 7 volts.

In certain examples of the above method, the cell is a parallel plate reactor. In certain examples, a bipolar configuration can be employed for multiple flow cells to be used in parallel.

In certain examples of the above method, the method proceeds for about 1 min, 2 min, 3 min, 5 min, 10 min, 20 min, 30 min, 40 min, 50 min, 1 hr, 2 hrs, 3 hrs, 4 hrs, 5 hrs, 6 hrs, 7 hrs, 8 hrs, 9 hrs, 10 hrs, 11 hrs, 12 hrs, 13 hrs, 14 hrs, 15 hrs, 20 hrs, 24 hrs, 25 hrs, 26 hrs, 27 hrs, 28 hrs, 29 hrs, 30 hrs, 36 hrs, 40 hrs, 48 hrs, 54 hrs, 60 hrs, 65 hrs, 68 hrs, 72 hrs, 80 hrs, 85 hrs, 90 hrs, 96 hrs, or 100 hrs.

In the above method, the inner diameter of the tubing employed in the electrochemical continuous flow system is sufficient to enable the generation of a diffusion layer on the surface of the electrode. In certain examples, this inner diameter is from about 1 mm to 5 cm. In certain examples, the inner diameters of the tubing employed in the continuous flow system is from 1 cm to 5 cm, 1 mm to 5 mm, 1 mm to 7 mm, 1 mm to 3 cm, or 2 mm to 1.5 cm. In examples, the inner diameter of the tubing is dependent on the overall size of the continuous flow setup. Without wishing to be bound by theory, it is understood that the salt is absorbed preferentially at the electrode surface, excluding water and forming a relatively hydrophobic reaction zone. As such, the diol has a favorable opportunity to form, rather than react with water, resulting in a higher selectivity for the diol over the alcohol. It is the hydrophobic layer, in conjunction with the ability to control the reactant flow, pH, temperature, and time of the reaction through the electrochemical continuous flow system, that enables the generation of 1,2-di(furan-2-yl)ethane-1,2-diol in higher chemoselectivity, stereoselectivity, yield, and purity than a batch method.

In certain examples of the above method, the method produces 1,2-di(furan-2-yl)ethane-1,2-diol in higher chemoselectivity than a batch method. In certain examples, the method produces 1,2-di(furan-2-yl)ethane-1,2-diol in greater chemoselectivity than a furfural alcohol, for example. In certain examples of the above method, the method produces 1,2-di(furan-2-yl)ethane-1,2-diol in 10%, 20%, 30%, 40%, 50%, 60%, 70%, 75%, 80%, 85%, 86%, 87%, 88%, 89%, 90%, 91%, 92%, 93%, 94%, 95%, 96%, 97%, 98%, or 99% greater chemoselectivity than a batch method. Non-liming methods to determine the chemoselectivity of the product include NMR, mass spectrometry, or gas or liquid chromatography.

In certain examples of the above method, the method produces 1,2-di(furan-2-yl)ethane-1,2-diol in higher purity than a batch method. In certain examples of the above method, the method produces 1,2-di(furan-2-yl)ethane-1,2-diol in 85%, 86%, 87%, 88%, 89%, 90%, 91%, 92%, 93%, 94%, 95%, 96%, 97%, 98%, 99%, or 100% purity. In certain examples of the above method, the method produces 1,2-di(furan-2-yl)ethane-1,2-diol in 10%, 20%, 30%, 40%, 50%, 60%, 70%, 80%, 90%, or 95% greater purity than a batch method. Non-limiting methods to determine the purity of the product include melting point, gas or liquid chromatography, mass spectroscopy, capillary electrophoresis, or optical rotation.

In certain examples of the above method, the method produces 1,2-di(furan-2-yl)ethane-1,2-diol in higher yield than a batch method. In certain examples of the above method, the method produces 1,2-di(furan-2-yl)ethane-1,2-diol in 40%, 50%, 60%, 70%, 80%, 90%, 91%, 92%, 93%, 94%, 95%, 96%, 97%, 98%, 99%, or 100% yield. In certain examples of the above method, the method produces 1,2-di (furan-2-yl)ethane-1,2-diol in 30%, 40%, 50%, 60%, 70%, 75%, 80%, 85%, 90%, 95%, 96%, 97%, 98%, or 99% greater than yield than a batch method. The percent yield can be determined by the following equation: % yield=(actual yield/theoretical yield)×100.

In an example of the electrochemical continuous flow system, the cathode is zinc, and the anode is steel. The static mixer is the cathode. The anode comprises the reaction tube wall. The electrolytic medium and initial electrolysis medium comprise furan-2-carbaldehyde, water, and an ammonium salt, wherein the salt is tetrabutylammonium phosphate. The amount of salt supplied is about 0.10% weight, which can maintain the diffusion layer. The reactants are electrolyzed at a current density of 20 A dm$^2$. The process proceeds at a temperature of about 5° C. The velocity of the velocity of circulation of the mixture is about 5 m/sec. The reaction proceeds for about one hour.

V. Electrochemical Continuous Flow System Assembly

In examples, the subject matter disclosed herein is directed to an electrochemical process comprising a static mixer. In certain examples, the process is for continuously preparing 1,2-di(furan-2-ypethane-1,2-diol from furan-2-carbaldehyde.

In certain examples, the subject matter disclosed herein is directed an electrochemical continuous flow system for reductively dimerizing furan-2-carbaldehyde to prepare 1,2-di(furan-2-yl)ethane-1,2-diol. In certain examples of the above system, the system comprises an electrolytic cell having an anode and a cathode in contact with an electrolytic medium. In certain examples of the above system, the system further comprises a static mixer. In certain examples, the static mixer is the cathode. In certain examples of the electrochemical continuous flow system, an annular tube reactor contains the cell, wherein surfaces of the annular tube reactor are the anode. In certain examples of the above system, the system further comprises a coolant. In certain examples, the coolant comprises ethylene or propylene glycol mixtures in water. In certain examples, the coolant is antifreeze.

Further, the disclosure comprises examples according to the following clauses:

Clause 1. A method for continuously preparing 1,2-di(furan-2-yl)ethane-1,2-diol from furan-2-carbaldehyde Clause 2. The method of Clause 1, wherein said method proceeds in a continuous flow system.

Clause 3. The method of Clause 1 or 2, comprising:
introducing a first reactant stream comprising said furan-2-carbaldehyde into a reactor column comprising a metal;
introducing a second reactant stream comprising a catalyst into said reactor column;
contacting said first reactant stream with said second reactant stream to form a mixture; and passing said mixture through said column to produce said 1,2-di(furan-2-yl)ethane-1,2-diol;
wherein said method proceeds in the presence of a solvent.

Clause 4. The method of Clause 3, wherein said reactor column comprising said metal comprises a packed bed comprising said metal.

Clause 5. The method of Clause 3, wherein said reactor column comprising a metal comprises a static mixer wherein said metal is deposited on surfaces of said static mixer.

Clause 6. The method of any of Clauses 3-5, wherein said metal is selected from the group consisting of Cu, Zn, Mn, Mg, Al, Ni, Pd, Rh, Ru, Co, and Pt.

Clause 7. The method of any of Clauses 3-6, wherein said metal is Zn.

Clause 8. The method of any of Clauses 3-7, wherein said solvent is selected from the group consisting of tetrahydrofuran, dichloromethane, toluene, acetonitrile, diethyl ether, methanol, and N,N-dimethylformamide.

Clause 9. The method of any of Clauses 3-8, wherein said catalyst is a transition metal salt or a rare earth metal salt.

Clause 10. The method of Clause 9, wherein said rare earth metal salt is a samarium salt.

Clause 11. The method of Clause 9, wherein said transition metal salt is a titanium salt.

Clause 12. The method of Clause 11, wherein said titanium salt is selected from the group consisting of $TiCl_4$, $TiBr_4$, $TiI_4$, $TiI_4$, di(cyclopentadienyl)titanium(IV) dichloride, and $TiCl_3$.

Clause 13. The method of Clause 12, wherein said titanium salt is $TiCl_4$.

Clause 14. The method of any of Clauses 3-13, wherein said method further comprises contacting said mixture with an ion exchange material.

Clause 15. The method of any of Clauses 3-14, wherein said method further comprises distilling said mixture.

Clause 16. The method of any of Clauses 3-15, wherein said mixture maintains a pH of about 3.

Clause 17. The method of any of Clauses 1-16, wherein said method proceeds at a temperature of about −10° C. to about 100° C.

Clause 18. The method of any of Clauses 3-17, wherein said reactor column has a pressure of about 1 atm to about 20 atm.

Clause 19. The method of any of Clauses 3-18, wherein said first reactant stream comprising said furan-2-carbaldehyde has a flow rate of about 0.01 L/min to about 1 L/min.

Clause 20. The method of any of Clauses 3-19, wherein said second reactant stream comprising said catalyst has a flow rate of about 0.01 L/min to about 1 L/min.

Clause 21. The method of any of Clauses 3-20, wherein the solvent is present in about 0.1 to about 20 volumes.

Clause 22. A continuous flow system for preparing 1,2-di(furan-2-yl)ethane-1,2-diol from furan-2-carbaldehyde.

Clause 23. The continuous flow system of Clause 22, wherein said system comprises: a first reactant stream comprising said furan-2-carbaldehyde; a second reactant stream comprising a catalyst; a solvent; and a reactor column comprising a metal.

Clause 24. The continuous flow system of Clause 22 or 23, further comprising a coolant.

Clause 25. The continuous flow system of Clause 23 or 24, wherein said reactor column comprising a metal comprises a static mixer, wherein said metal is deposited on surfaces of said static mixer.

Clause 26. The continuous flow system of any of Clauses 23-25, wherein said reactor column comprising a metal comprises a packed bed comprising said metal.

Clause 27. The continuous flow system of any of Clauses 22-26, further comprising a column comprising an ion exchange material.

Clause 28. The method of Clause 1, wherein said method proceeds by an electrochemical process.

Clause 29. The method of Clause 28, wherein said electrochemical process comprises reductively dimerizing furan-2-carbaldehyde to prepare 1,2-di(furan-2-ypethane-1,2-diol by passing a direct electrical current through an electrolytic cell having an anode and a cathode in contact with an electrolytic medium.

Clause 30. The method of Clause 29, wherein said electrolytic medium comprises an initial electrolysis medium comprising furan-2-carbaldehyde, water, and at least one salt.

Clause 31. The method of Clause 30, wherein said at least one salt is selected from the group consisting of sodium, potassium, lithium, and ammonium.

Clause 32. The method of Clause 29, where an amount of base or acid is added to said medium to maintain a pH of about 2 to about 5.

Clause 33. The method of Clause 29 or 32, where an amount of base or acid is added to said medium to maintain a pH of about 3.

Clause 34. The method of any of Clauses 29-33, further comprising a static mixer.

Clause 35. The method of Clause 34, wherein said static mixer is said cathode.

Clause 36. The method of any of Clauses 29-35, wherein an annular tube reactor contains said cell, wherein surfaces of said annular tube reactor are said anode.

Clause 37. The method of any of Clauses 28-36, wherein said electrochemical process proceeds at a temperature of about −30° C. to 150° C.

Clause 38. The method of any of Clauses 29-37, wherein said cell is a parallel plate reactor.

Clause 39. An electrochemical process comprising a static mixer.

Clause 40. The electrochemical process of Clause 39, wherein said process is for continuously preparing 1,2-di(furan-2-yl)ethane-1,2-diol from furan-2-carbaldehyde.

Clause 41. An electrochemical continuous flow system for reductively dimerizing furan-2-carbaldehyde to prepare 1,2-di(furan-2-yl)ethane-1,2-diol.

Clause 42. The electrochemical continuous flow system of Clause 41, wherein said system comprises an electrolytic cell having an anode and a cathode in contact with an electrolytic medium.

Clause 43. The electrochemical continuous flow system of Clause 41 or 42, further comprising a static mixer.

Clause 44. The electrochemical continuous flow system of Clause 43, wherein said static mixer is said cathode.

Clause 45. The method of any of Clauses 1-21 or 28-38, wherein said method produces said 1,2-di(furan-2-yl)ethane-1,2-diol in higher stereoselectivity than a batch method.

Clause 46. The method of any of Clauses 1-21 or 28-38, wherein said method produces said 1,2-di(furan-2-yl)ethane-1,2-diol in higher chemoselectivity than a batch method.

Clause 47. The method of any of Clauses 1-21 or 28-38, wherein said method produces said 1,2-di(furan-2-yl)ethane-1,2-diol in higher purity than a batch method.

Clause 48. The method of any of Clauses 1-21 or 28-38, wherein said method produces said 1,2-di(furan-2-yl)ethane-1,2-diol in higher yield than a batch method.

The following examples are offered by way of illustration and not by way of limitation.

EXAMPLES

Example 1

Chemical Continuous Flow Example

A mixture containing furfural in toluene enters the first reaction stream into a continuous flow chemical reactor. The pressure of the reactor is set to 16 psi. A second stream comprising $TiCl_4$ in toluene enters the reactor. The amount of $TiCl_4$ introduced to the reactor is about 1/100 or less of the furfural concentration. The two streams are mixed inside the reactor with the assistance of a static mixer. The static mixer has zinc metal deposited on the plates of the mixer. The reactor contains a coolant that maintains the temperature of the reaction mixture at about 0° C. The coolant comprises a mixture of ethylene glycol and water. After approximately thirty minutes of mixing, the reaction mixture is fed through a column comprising a sulfonic acid cation exchange resin to remove the Zn metal from the mixture. Following this, the mixture undergoes vacuum distillation to provide the desired 1,2-di(furan-2-yl)ethane-1,2-diol product in 99% yield. The purity of the product is 99% pure as determined by HPLC.

Example 2

Electrochemical Continuous Flow Example

Figure 4:
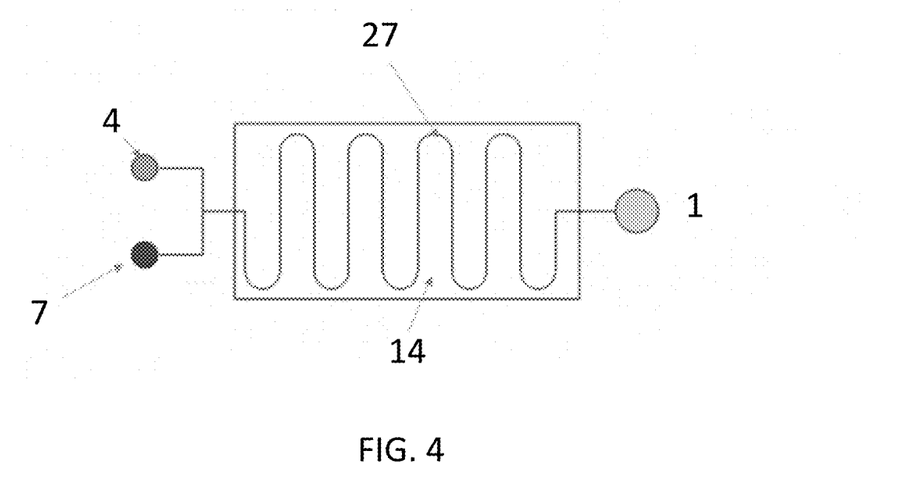
FIG. 4 shows a schematic of a continuous flow electrochemical annular reactor described herein.

Use is made of an annular electrochemical reactor comprising cells connected in parallel. The cells comprises a zinc cathode and a steel anode. Each of the cells has an electrolyte inset and an electrolyte outlet. The reactor apparatus further comprises a static mixer, which is the cathode. The anode is the reaction tube wall. An emulsion, as an electrolyte, consisting of furfural, ammonium phosphate, water, and potassium phosphate is charged into the reactor. $TiCl_4$ is also charged into the reactor by means of a separate input (See FIG. 4). The reactants, including the emulsion, are electrolyzed at a current density of 20 A $dm^2$. The static mixer mixes the reaction mixture at a flow rate of about 100 ml/minute. The reaction is maintained at a temperature of about 5° C. with the help of a coolant. The coolant comprises a mixture of ethylene glycol and water. After one hour of reaction, it is determined that 1,2-di(furan-2-ypethane-1,2-diol is produced in about 98% yield. The product is 99% pure as determined by HPLC.

Example 3

Comparative Batch Method Example

A 100 mL Pyrex flask is charged with furfural (1 mmol), Zn powder (0.5 g), THF (10 mL), and $TiCl_4$. The reactants are mixed together, cooled to 0° C., and allowed to dwell for three hours. The mixture is extracted with ethyl acetate (3×15 mL). The combined organic layers are washed with saturated aqueous $NaHCO_3$ solution and brine, dried over magnesium sulfate, and filtered. The filtrate is concentrated in vacuous to give a crude material, which is separated by column chromatography on silica (200-300 mesh), and eluted with petroleum ether. The reaction produces a mixture containing 1,2-di(furan-2-yl)ethane-1,2-diol in 50% yield and furan-2-ylmethanol in 45% yield, with approximately 5% of the product mixture comprising unreacted furfural starting material.

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Throughout this specification and the claims, the words "comprise," "comprises," and "comprising" are used in a non-exclusive sense, except where the context requires otherwise. It is understood that examples described herein include "consisting of" and/or "consisting essentially of" examples.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other examples set forth herein will come to mind to one skilled in the art to which this subject matter pertains having the benefit of the teachings presented in the foregoing descriptions and the associated drawings. Therefore, it is to be understood that the subject matter is not to be limited to the specific examples disclosed and that modifications and other examples are intended to be included within the scope of the appended claims. Although specific terms are employed herein, they are used in a generic and descriptive sense only and not for purposes of limitation.

What is claimed is:

1. A method for continuously preparing 1,2-di(furan-2-yl)ethane-1,2-diol from furan-2-carbaldehyde:

the method comprising:
introducing a first reactant stream comprising said furan-2-carbaldehyde;
introducing a second reactant stream comprising a catalyst salt, the catalyst salt introduced at a concentration of about 1/100 or less of a concentration of the furan-2-carbaldehyde;
contacting said first reactant stream with said second reactant stream to form a mixture; and
passing said mixture through a sacrificial reactor column to produce said 1,2-di(furan-2-yl)ethane-1,2-diol, the sacrificial reactor column comprising a metal,
wherein said method proceeds in the presence of a solvent, and
wherein said method produces the 1,2-di(furan-2-yl)ethane-1,2-diol in at least 90% yield.

2. The method of claim 1, wherein said method proceeds in a continuous flow system.

3. The method of claim 1, wherein said sacrificial reactor column comprises a packed bed comprising said metal.

4. The method of claim 1, wherein said sacrificial reactor column comprises a static mixer, and wherein said metal is deposited on surfaces of said static mixer.

5. The method of claim 3, wherein said catalyst salt is a transition metal salt.

6. The method of claim 3, wherein subsequent to passing said mixture through the sacrificial reactor column, said method further comprises contacting said mixture with an ion exchange material.

7. The method of claim 3, wherein said metal is selected from the group consisting of Cu, Zn, Mn, Mg, Al, Ni, Pd, Rh, Ru, Co, and Pt.

8. The method of claim 7, wherein said metal is Zn.

9. The method of claim 3, wherein said solvent is selected from the group consisting of tetrahydrofuran, dichloromethane, toluene, acetonitrile, diethyl ether, methanol, and N,N-dimethylformamide.

10. The method of claim 1, wherein said catalyst salt is a samarium salt.

11. The method of claim 5, wherein said transition metal salt is a titanium salt.

12. The method of claim 11, wherein said titanium salt is selected from the group consisting of $TiCl_4$, $TiBr_4$, $TiI_4$, di(cyclopentadienyl)titanium(IV) dichloride, and $TiCl_3$.

13. The method of claim 12, wherein said titanium salt is $TiCl_4$.

14. The method of claim 3, wherein said method further comprises distilling said mixture.

15. A method for continuously preparing 1,2-di(furan-2-yl)ethane-1,2-diol from furan-2-carbaldehyde:

the method comprising:
introducing a first reactant stream comprising said furan-2-carbaldehyde;
introducing a second reactant stream comprising a catalyst salt;
contacting said first reactant stream with said second reactant stream to form a mixture; and
passing said mixture through a reactor column to produce said 1,2-di(furan-2-yl)ethane-1,2-diol,
wherein said method proceeds by an electrochemical process.

16. The method of claim 15, wherein said electrochemical process comprises reductively dimerizing furan-2-carbaldehyde to prepare 1,2-di(furan-2-yl)ethane-1,2-diol by passing a direct electrical current through an electrolytic cell having an anode and a cathode in contact with an electrolytic medium.

17. The method of claim 16, wherein said electrolytic medium comprises an initial electrolysis medium comprising the furan-2-carbaldehyde, water, and at least one salt.

18. The method of claim 16, wherein said cathode is a static mixer.

19. The method of claim 16, wherein an annular tube reactor contains said electrolytic cell, wherein surfaces of said annular tube reactor are said anode.

20. The method of claim 16, wherein said electrolytic cell is a parallel plate reactor.

21. The method of claim 15, wherein the reactor column comprises a static mixer and wherein passing said mixture through the reactor column comprises:
mixing the mixture at a flow rate of about 100 ml/minute.

* * * * *

UNITED STATES PATENT AND TRADEMARK OFFICE
CERTIFICATE OF CORRECTION

PATENT NO. : 12,234,213 B2
APPLICATION NO. : 17/370697
DATED : February 25, 2025
INVENTOR(S) : Patrick J. Kinlen and William F. Lyons It is certified that error appears in the above-identified patent and that said Letters Patent is hereby corrected as shown below:

In the Claims

Column 17 Claim 5, Line 51, after "claim" delete "3".
Column 17 Claim 5, Line 51, after "claim" insert --1--.
Column 17 Claim 6, Line 53, after "claim" delete "3".
Column 17 Claim 6, Line 53, after "claim" insert --1--.
Column 17 Claim 7, Line 56, after "claim" delete "3".
Column 17 Claim 7, Line 56, after "claim" insert --1--.
Column 18 Claim 9, Line 2, after "claim" delete "3".
Column 18 Claim 9, Line 2, after "claim" insert --1--.
Column 18 Claim 14, Line 15, after "claim" delete "3".
Column 18 Claim 14, Line 15, after "claim" insert --1--.

Signed and Sealed this
Twenty-ninth Day of April, 2025

Coke Morgan Stewart
*Acting Director of the United States Patent and Trademark Office*